(12) United States Patent
Hodgkinson

(10) Patent No.: US 9,107,667 B2
(45) Date of Patent: Aug. 18, 2015

(54) SURGICAL STAPLING APPARATUS INCLUDING RELEASABLE BUTTRESS

(71) Applicant: Covidien LP, Mansfield, MA (US)

(72) Inventor: Gerald Hodgkinson, Guilford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/569,918

(22) Filed: Dec. 15, 2014

(65) Prior Publication Data

US 2015/0097018 A1    Apr. 9, 2015

Related U.S. Application Data

(63) Continuation of application No. 14/523,998, filed on Oct. 27, 2014, which is a continuation of application No. 14/075,087, filed on Nov. 8, 2013, now Pat. No. 8,870,050, which is a continuation of application No. 13/289,197, filed on Nov. 4, 2011, now Pat. No. 8,584,920.

(51) Int. Cl.
| A61B 17/068 | (2006.01) |
| A61B 17/072 | (2006.01) |
| A61B 17/10 | (2006.01) |
| A61B 17/115 | (2006.01) |
| A61B 17/00 | (2006.01) |

(52) U.S. Cl.
CPC ............ *A61B 17/105* (2013.01); *A61B 17/0682* (2013.01); *A61B 17/072* (2013.01); *A61B 17/07292* (2013.01); *A61B 17/115* (2013.01); *A61B 2017/00526* (2013.01); *A61B 2017/07271* (2013.01)

(58) Field of Classification Search
CPC ........... A61B 17/07292; A61B 17/072; A61B 17/068; A61B 17/1155
USPC .............................. 227/175.1, 176.1; 606/151
See application file for complete search history.

(56) References Cited

U.S. PATENT DOCUMENTS

| 3,054,406 A | 9/1962 | Usher |
| 3,079,606 A | 3/1963 | Bobrov et al. |
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |

(Continued)

FOREIGN PATENT DOCUMENTS

| DE | 19924311 A1 | 11/2000 |
| EP | 0 327 022 A2 | 8/1989 |

(Continued)

OTHER PUBLICATIONS

European Search Report corresponding to EP 05 02 2585.3, completed Jan. 25, 2006 and mailed Feb. 3, 2006; (4 pp).

(Continued)

*Primary Examiner* — Michelle Lopez

(57) ABSTRACT

A staple cartridge for use with a surgical stapling apparatus includes a cartridge body, a plurality of staples disposed within the cartridge body, a tissue contacting surface on the cartridge body defining staple retaining slots dimensioned to releasably retain a staple, and a buttress material including at least one weld joining the buttress material to the tissue contacting surface of the cartridge body. The at least one weld is positioned to at least partially overlie a staple retaining slot.

21 Claims, 11 Drawing Sheets

(56) References Cited

U.S. PATENT DOCUMENTS

| | | |
|---|---|---|
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 * | 12/2001 | Hamilton et al. ............ 606/151 |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,590,095 B1 | 7/2003 | Schleicher et al. |
| 6,592,597 B2 | 7/2003 | Grant et al. |
| 6,605,294 B2 | 8/2003 | Sawhney |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,009,034 B2 | 3/2006 | Pathak et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,141,055 B2 | 11/2006 | Abrams et al. |
| 7,147,138 B2 | 12/2006 | Shelton, IV |
| 7,160,299 B2 | 1/2007 | Baily |
| 7,232,449 B2 | 6/2007 | Sharkawy et al. |
| 7,241,300 B2 | 7/2007 | Sharkawy et al. |
| 7,247,338 B2 | 7/2007 | Pui et al. |

(56) References Cited

U.S. PATENT DOCUMENTS

| | | | |
|---|---|---|---|
| 7,279,322 B2 | 10/2007 | Pui et al. |
| 7,307,031 B2 | 12/2007 | Carroll et al. |
| 7,311,720 B2 | 12/2007 | Mueller et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,649,089 B2 | 1/2010 | Kumar et al. |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 * | 5/2011 | Bettuchi .................. 227/179.1 |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,028,883 B2 | 10/2011 | Stopek |
| 8,033,483 B2 | 10/2011 | Fortier et al. |
| 8,038,045 B2 | 10/2011 | Bettuchi et al. |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,408,440 B2 | 4/2013 | Olson et al. |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,584,920 B2 | 11/2013 | Hodgkinson |
| 8,590,762 B2 | 11/2013 | Hess et al. |
| 8,616,430 B2 | 12/2013 | Stopek et al. |
| 8,631,989 B2 | 1/2014 | Aranyi et al. |
| 8,668,129 B2 | 3/2014 | Olson |
| 8,684,250 B2 | 4/2014 | Bettuchi et al. |
| 8,870,050 B2 | 10/2014 | Hodgkinson |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 2002/0028243 A1 | 3/2002 | Masters |
| 2002/0086990 A1 | 7/2002 | Kumar et al. |
| 2002/0091397 A1 | 7/2002 | Chen |
| 2002/0165559 A1 * | 11/2002 | Grant et al. .................. 606/139 |
| 2003/0065345 A1 | 4/2003 | Weadock |
| 2003/0078209 A1 | 4/2003 | Schmidt |
| 2003/0083676 A1 | 5/2003 | Wallace |
| 2003/0181927 A1 | 9/2003 | Wallace |
| 2003/0183671 A1 | 10/2003 | Mooradian et al. |
| 2003/0208231 A1 | 11/2003 | Williamson et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0131225 A1 | 6/2005 | Kumar et al. |
| 2005/0149073 A1 | 7/2005 | Arani et al. |
| 2005/0154093 A1 | 7/2005 | Kwon et al. |
| 2006/0004407 A1 | 1/2006 | Hiles et al. |
| 2006/0008505 A1 | 1/2006 | Brandon |
| 2006/0093672 A1 | 5/2006 | Kumar et al. |
| 2006/0121266 A1 | 6/2006 | Fandel et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0054880 A1 | 3/2007 | Saferstein et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |

(56) References Cited

U.S. PATENT DOCUMENTS

| | | |
|---|---|---|
| 2007/0213522 A1 | 9/2007 | Harris et al. |
| 2007/0237741 A1 | 10/2007 | Figuly et al. |
| 2007/0237742 A1 | 10/2007 | Figuly et al. |
| 2007/0243227 A1 | 10/2007 | Gertner |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0164440 A1 | 7/2008 | Maase et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0194805 A1 | 8/2008 | Vignon et al. |
| 2008/0200949 A1 | 8/2008 | Hiles et al. |
| 2008/0214695 A1 | 9/2008 | Pathak et al. |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0220560 A1 | 9/2009 | Wan et al. |
| 2009/0263441 A1 | 10/2009 | McKay |
| 2009/0277947 A1 | 11/2009 | Viola |
| 2009/0287230 A1 | 11/2009 | D'Agostino et al. |
| 2010/0012704 A1 | 1/2010 | Racenet et al. |
| 2010/0065606 A1 | 3/2010 | Stopek |
| 2010/0065607 A1 | 3/2010 | Orban, III et al. |
| 2010/0065660 A1 | 3/2010 | Hull et al. |
| 2010/0072254 A1 | 3/2010 | Aranyi et al. |
| 2010/0096481 A1 | 4/2010 | Hull et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0082427 A1 | 4/2011 | Golzarian et al. |
| 2011/0087279 A1 | 4/2011 | Shah et al. |
| 2011/0089375 A1 | 4/2011 | Chan et al. |
| 2011/0293690 A1 | 12/2011 | Griffin et al. |
| 2012/0156289 A1 | 6/2012 | Blaskovich et al. |
| 2012/0187179 A1 | 7/2012 | Gleiman |
| 2012/0273547 A1 | 11/2012 | Hodgkinson et al. |
| 2013/0037596 A1 | 2/2013 | Bear et al. |
| 2013/0105548 A1 | 5/2013 | Hodgkinson et al. |
| 2013/0105553 A1 | 5/2013 | Racenet et al. |
| 2013/0112732 A1 | 5/2013 | Aranyi et al. |
| 2013/0112733 A1 | 5/2013 | Aranyi et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0181031 A1 | 7/2013 | Olson et al. |
| 2013/0193186 A1 | 8/2013 | Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0277411 A1 | 10/2013 | Hodgkinson et al. |
| 2013/0306707 A1 | 11/2013 | Viola et al. |
| 2013/0310873 A1 | 11/2013 | Stopek et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |

FOREIGN PATENT DOCUMENTS

| | | |
|---|---|---|
| EP | 0 594 148 A1 | 4/1994 |
| EP | 0 667 119 A1 | 8/1995 |
| EP | 1 064 883 A1 | 1/2001 |
| EP | 1 256 317 A2 | 11/2002 |
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 A1 | 8/2007 |
| EP | 1 929 958 A2 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 090 231 A1 | 8/2009 |
| EP | 2 090 244 A2 | 8/2009 |
| EP | 2 090 252 A2 | 8/2009 |
| EP | 2 198 787 A1 | 6/2010 |
| EP | 2 236 098 A2 | 10/2010 |
| EP | 2 292 276 A2 | 3/2011 |
| EP | 2 311 386 A2 | 4/2011 |
| EP | 2 462 880 A2 | 6/2012 |
| EP | 2 517 637 A1 | 10/2012 |
| EP | 2 620 105 A1 | 7/2013 |
| EP | 2 620 106 A2 | 7/2013 |
| EP | 2 630 922 A1 | 8/2013 |
| EP | 2 644 125 A2 | 10/2013 |

(56) References Cited

FOREIGN PATENT DOCUMENTS

| | | |
|---|---|---|
| EP | 2 762 091 A2 | 8/2014 |
| JP | 2000-166933 A | 6/2000 |
| JP | 2002-202213 A | 7/2002 |
| JP | 2007-124166 A | 5/2007 |
| WO | 90/05489 A1 | 5/1990 |
| WO | 95/16221 A1 | 6/1995 |
| WO | 96/22055 A1 | 7/1996 |
| WO | 97/01989 A1 | 1/1997 |
| WO | 97/13463 A1 | 4/1997 |
| WO | 98/17180 A1 | 4/1998 |
| WO | 99/45849 A1 | 9/1999 |
| WO | 03/088845 A2 | 10/2003 |
| WO | 03082126 A1 | 10/2003 |
| WO | 03/094743 A1 | 11/2003 |
| WO | 03/105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |
| WO | 2010075298 A2 | 7/2010 |
| WO | 2011143183 A2 | 11/2011 |
| WO | 2012044848 A1 | 4/2012 |

OTHER PUBLICATIONS

European Search Report corresponding to EP 06 00 4598, completed Jun. 22, 2006; (2 pp).
European Search Report corresponding to EP 06 01 6962.0, completed Jan. 3, 2007 and mailed Jan. 11, 2007; (10 pp).
International Search Report corresponding to International Application No. PCT/US2005/036740, completed Feb. 20, 2007 and mailed Mar. 23, 2007; (8 pp).
International Search Report corresponding to International Application No. PCT/US2007/022713, completed Apr. 21, 2008 and mailed May 15, 2008; (1 p).
International Search Report corresponding to International Application No. PCT/US2008/002981, completed Jun. 9, 2008 and mailed Jun. 26, 2008; (2 pp).
European Search Report corresponding to EP 08 25 1779, completed Jul. 14, 2008 and mailed Jul. 23, 2008; (5 pp).
European Search Report corresponding to EP 08 25 1989.3, completed Mar. 11, 2010 and mailed Mar. 24, 2010; (6 pp).
European Search Report corresponding to EP 10 25 0639.1, completed Jun. 17, 2010 and mailed Jun. 28, 2010; (7 pp).
European Search Report corresponding to EP 10 25 0715.9, completed Jun. 30, 2010 and mailed Jul. 20, 2010; (3 pp).
European Search Report corresponding to EP 05 80 4382.9, completed Oct. 5, 2010 and mailed Oct. 12, 2010; (3 pp).
European Search Report corresponding to EP 10 25 1437.9, completed Nov. 22, 2010 and mailed Dec. 16, 2010; (3 pp).
European Search Report corresponding to EP 09 25 2897.5, completed Feb. 7, 2011 and mailed Feb. 15, 2011; (3 pp).
European Search Report corresponding to EP 10 25 0642.5, completed Mar. 25, 2011 and mailed Apr. 4, 2011; (4 pp).
European Search Report corresponding to EP 11 18 8309.6, completed Dec. 15, 2011 and mailed Jan. 12, 2012; (3 pp).
European Search Report corresponding to EP 12 15 2229.6, completed Feb. 23, 2012 and mailed Mar. 1, 2012; (4 pp).
European Search Report corresponding to EP 12 15 0511.9, completed Apr. 16, 2012 and mailed Apr. 24, 2012; (7 pp).
European Search Report corresponding to EP 12 15 2541.4, completed Apr. 23, 2012 and mailed May 3, 2012; (10 pp).
European Search Report corresponding to EP 12 16 5609.4, completed Jul. 5, 2012 and mailed Jul. 13, 2012; (8 pp).
European Search Report corresponding to EP 12 15 8861.0, completed Jul. 17, 2012 and mailed Jul. 24, 2012; (9 pp).
European Search Report corresponding to EP 12 16 5878.5, completed Jul. 24, 2012 and mailed Aug. 6, 2012; (8 pp).
Extended European Search Report corresponding to EP 12 19 1035.0, completed Jan. 11, 2013 and mailed Jan. 18, 2013; (7 pp).
Extended European Search Report corresponding to EP 12 18 6175.1, completed Jan. 15, 2013 and mailed Jan. 23, 2013; (7 pp).
Extended European Search Report corresponding to EP 12 19 1114.3, completed Jan. 23, 2013 and mailed Jan. 31, 2013; (10 pp).
Extended European Search Report corresponding to EP 12 19 2224.9, completed Mar. 14, 2013 and mailed Mar. 26, 2013; (8 pp).
Extended European Search Report corresponding to EP 12 19 6904.2, completed Mar. 28, 2013 and mailed Jul. 26, 2013; (8 pp).
Extended European Search Report corresponding to EP 12 19 6911.7, completed Apr. 18, 2013 and mailed Apr. 24, 2013; (8 pp).
Extended European Search Report corresponding to EP 07 00 5842.5, completed May 13, 2013 and mailed May 29, 2013; (7 pp).
Extended European Search Report corresponding to EP 12 19 8776.2, completed May 16, 2013 and mailed May 27, 2013; (8 pp).
Extended European Search Report corresponding to EP 12 19 8749.9, completed May 21, 2013 and mailed May 31, 2013; (8 pp).
Extended European Search Report corresponding to EP 13 15 6297.7, completed Jun. 4, 2013 and mailed Jun. 13, 20131; (7 pp).
Extended European Search Report corresponding to EP 13 17 3985.6, completed Aug. 19, 2013 and mailed Aug. 28, 2013; (6 pp).
Extended European Search Report corresponding to EP 13 17 3986.4, completed Aug. 20, 2013 and mailed Aug. 29, 2013; (6 pp).
Extended European Search Report corresponding to EP 13 17 7437.4, completed Sep. 11, 2013 and mailed Sep. 19, 2013; 6 pages.
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and mailed Sep. 17, 2014; (8 pp).
Extended European Search Report corresponding to EP 14 16 8904.2, completed Sep. 10, 2014 and mailed Sep. 18, 2014; (8 pp).
Extended European Search Report corresponding to EP 13 19 4995.0, completed Jun. 5, 2014 and mailed Oct. 13, 2014; (10 pp).
Extended European Search Report corresponding to EP 13 15 4571.7, completed Oct. 10, 2014 and mailed Oct. 20, 2014; (8 pp).
Extended European Search Report corresponding to EP 14 18 1125.7, completed Oct. 16, 2014 and mailed Oct. 24, 2014; (7 pp).
Extended European Search Report corresponding to EP 14 18 1127.3, completed Oct. 16, 2014 and mailed Nov. 10, 2014; (8 pp).
Extended European Search Report corresponding to EP 14 19 0419.3, completed Mar. 24, 2015 and mailed Mar. 30, 2015; (6 pp).

\* cited by examiner

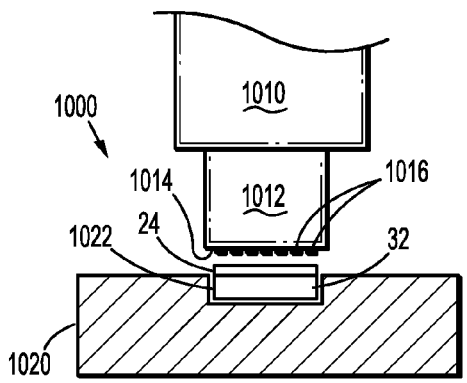
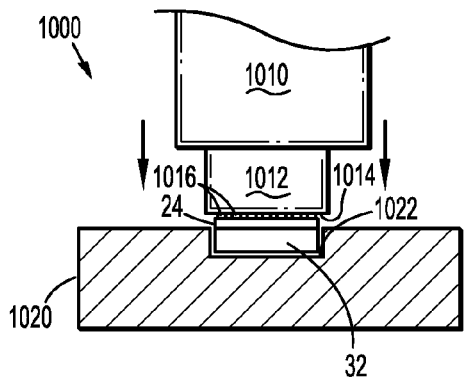
FIG. 4A　　FIG. 4B
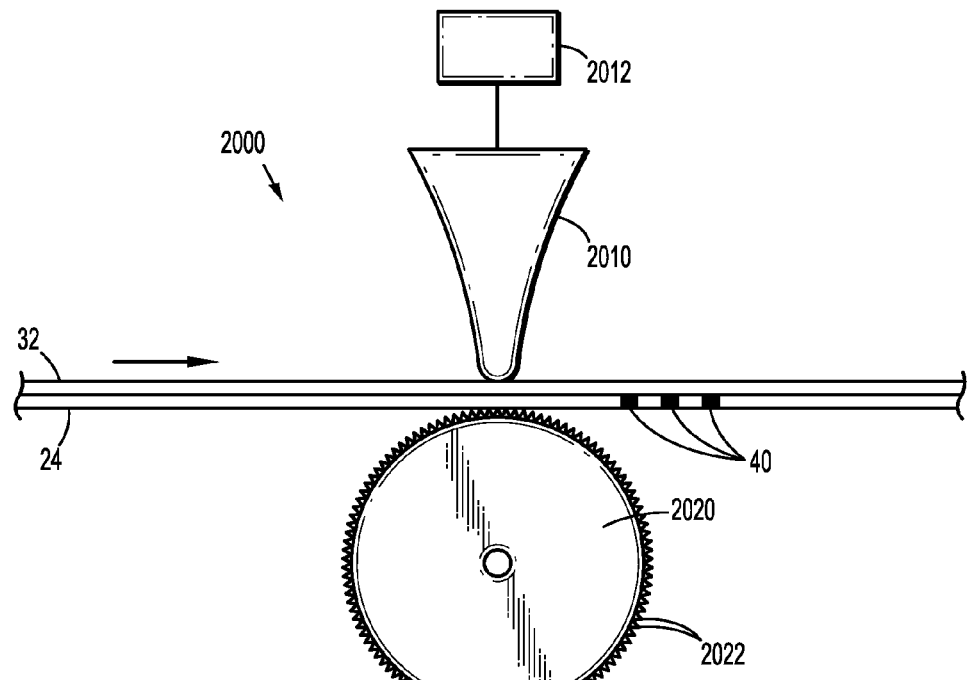
FIG. 5

SURGICAL STAPLING APPARATUS INCLUDING RELEASABLE BUTTRESS

CROSS-REFERENCE TO RELATED APPLICATIONS

This application is a continuation of U.S. patent application Ser. No. 14/523,998, filed Oct. 27, 2014, which is a continuation of U.S. patent application Ser. No. 14/075,087, filed Nov. 8, 2013, now U.S. Pat. No. 8,870,050, which is a continuation of U.S. patent application Ser. No. 13/289,197, filed Nov. 4, 2011, now U.S. Pat. No. 8,584,920, and the disclosures of each of the above-identified applications are hereby incorporated by reference in their entirety.

BACKGROUND

1. Technical Field

The present disclosure relates to surgical stapling apparatus including surgical buttresses which can be releasably attached to the surgical stapling apparatus, and in particular, to surgical stapling apparatus having surgical buttresses including at least one weld joining the buttress to the surgical stapling apparatus over an ejection path of a leg of a staple such that the buttress is released upon firing of the surgical stapling apparatus.

2. Background of Related Art

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the stapling apparatus is actuated, or "fired", longitudinally moving firing bars contact staple drive members in one of the jaws. The staple drive members push the surgical staples through the body tissue and into an anvil in the opposite jaw which forms the staples. If tissue is to be removed or separated, a knife blade can be provided in the jaws of the apparatus to cut the tissue between the lines of staples.

A number of surgical stapling apparatus rely on a knife blade cutting of some portion of the buttress to affect buttress release. These methods typically employ a secondary material or mounting structure in addition to the buttress material (e.g., sutures) to provide attachment of the buttress to the surgical stapling apparatus. Typically, firing forces are increased with each material that must be transected by the knife blade in order to release the buttress.

It would be desirable to provide a buttress that may be releasably secured to a surgical stapling apparatus without the need for a secondary material or mounting structure, and without the need for a knife blade to cut the buttress and/or secondary material or mounting structure to release the buttress from the surgical stapling apparatus, thereby resulting in the use of fewer materials and lower firing forces.

SUMMARY

According to an aspect of the present disclosure, a staple cartridge for use with a surgical stapling apparatus includes a cartridge body, a plurality of staples disposed within the cartridge body, a tissue contacting surface on the cartridge body defining staple retaining slots dimensioned to releasably retain staples, and a buttress material including at least one weld joining the buttress material to the tissue contacting surface. The at least one weld is positioned to at least partially overlie a staple retaining slot.

In embodiments, the at least one weld is dimensioned to extend at least partially over an ejection path of a leg of staple disposed in the staple retaining slot.

The buttress material may include a plurality of welds positioned at least partially over the staple retaining slots of the tissue contacting surface. In embodiments, the buttress material includes a plurality of welds positioned at least partially over a portion of all of the staple retaining slots of the tissue contacting surface. The plurality of welds may be distributed in a pattern over the tissue contacting surface.

The buttress material may be porous, non-porous, or combinations thereof. In embodiments, the buttress material is porous. In other embodiments, a portion of the buttress material, including the at least one weld, is non-porous.

The staple retaining slots may linearly extend along a length of the tissue contacting surface. Alternatively, the staple retaining slots may be in an annular or curved configuration. In embodiments, the tissue contacting surface includes at least two rows of staple retaining slots. The at least two row of staple retaining slots may be positioned in one of a linear configuration and an annular configuration. The buttress material may include a plurality of welds overlying at least one row of the staple retaining slots of the tissue contacting surface.

According to another aspect of the present disclosure, a surgical stapling apparatus including a releasable buttress material includes a cartridge assembly including a plurality of staples and a tissue contacting surface defining staple retaining slots, an anvil assembly including a tissue contacting surface defining staple pockets for forming staples expelled from the staple retaining slots of the cartridge assembly, and a buttress material including at least one weld joining the buttress material to the tissue contacting surface of the cartridge assembly. The at least one weld is positioned to at least partially overlie a staple retaining slot of the cartridge assembly.

In embodiments, the at least one weld is dimensioned to extend at least partially over an ejection path of a leg of a staple disposed in the staple retaining slot.

The buttress material may include a plurality of welds positioned at least partially over the staple retaining slots of the cartridge assembly. In embodiments, the buttress material includes a plurality of welds positioned at least partially over a portion of all of the staple retaining slots of the cartridge assembly. The plurality of welds may be distributed in a pattern over the tissue contacting surface of the cartridge assembly.

A buttress material may also be attached to the tissue contacting surface of the anvil assembly. The buttress material of the anvil assembly may be the same as, or different from, the buttress material of the cartridge assembly.

The buttress material may be porous, non-porous, or combinations thereof. In embodiments, the buttress material is porous. In other embodiments, a portion of the buttress material, including the at least one weld, is non-porous.

In embodiments, the cartridge assembly is associated with a first jaw and the anvil assembly is associated with a second jaw. The first and second jaws are selectively movable relative to one another from a first spaced apart position to a second position wherein the first and second jaws cooperate to grasp tissue therebetween. In such embodiments, the staple retaining slots and the staple pockets may linearly extend along a length of the cartridge assembly and the anvil assembly, respectively. The tissue contacting surfaces of the cartridge assembly and the anvil assembly may also include at least two rows of staple retaining slots and staple pockets, respectively. The buttress material of the cartridge assembly may include a plurality of welds overlying at least one row of the staple retaining slots of the cartridge assembly.

In embodiments, the cartridge assembly may be associated with a body portion of the surgical stapling apparatus and the anvil assembly includes a shaft removably mountable to the body portion, the anvil assembly being movable toward and away from the body portion. In such embodiments, the buttress material may include a plurality of welds in an annular configuration. The cartridge assembly and the anvil assembly may also include at least two annular rows of staple retaining slots and staple pockets. The buttress material of the cartridge assembly may include a plurality of welds overlying at least one row of the staple retaining slots of the cartridge assembly.

BRIEF DESCRIPTION OF THE DRAWINGS

Embodiments of the presently disclosed surgical stapling apparatus and surgical buttress are described herein with reference to the accompanying drawings, wherein:

FIGS. 4A and 4B are cross-sectional views of a staple cartridge of the surgical stapling apparatus and a surgical buttress in a pre-welded (FIG. 4A) and a post-welded (FIG. 4B) configuration in accordance with an exemplary process of forming the welds in accordance with an embodiment of the present disclosure;

FIG. 5 is a schematic view illustrating another exemplary process of forming the welds in accordance with another embodiment of the present disclosure;

DETAILED DESCRIPTION OF THE EMBODIMENTS

Figure 1:
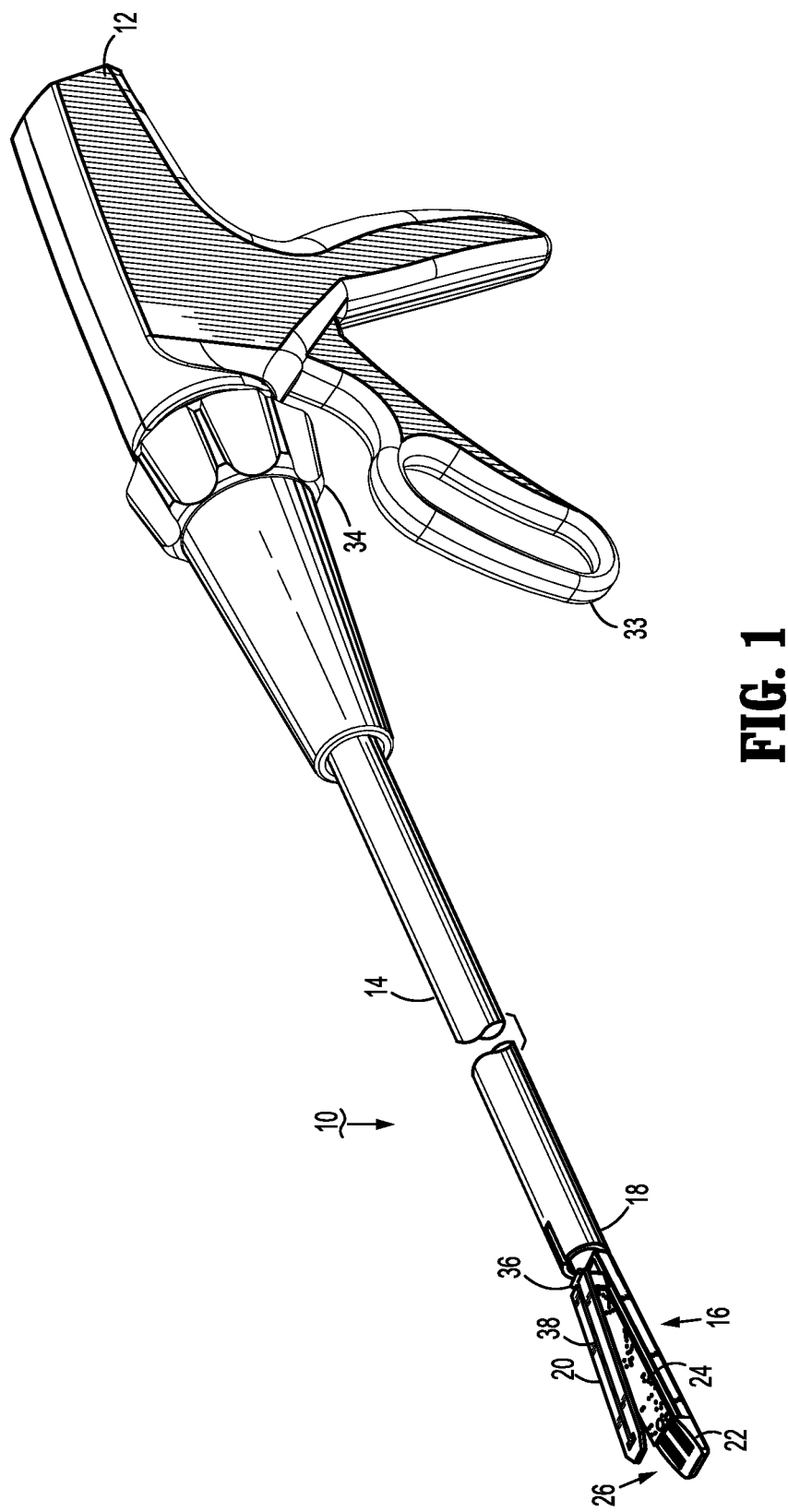
FIG. 1 is a perspective view of an illustrative embodiment of a surgical stapling apparatus including a surgical buttress in accordance with an embodiment of the present disclosure.

Various exemplary embodiments of the present disclosure are discussed herein below in terms of buttresses for use with surgical stapling apparatus. The buttresses described herein may be used in sealing a wound by approximating the edges of wound tissue between a staple cartridge and an anvil of a surgical stapling apparatus which contains at least one buttress. The at least one buttress is joined to the surgical stapling apparatus by at least one weld positioned at least partially within and/or across an ejection path of a staple. Firing of the surgical stapling apparatus forces the legs of at least one staple to pass through the opening on the staple cartridge, the at least one weld and the buttress, the tissue, and the openings on the anvil to secure the buttress to the tissue, to secure the adjoining tissue to one another, and to seal the tissue. The firing force of the staple impacts the weld and applies a force thereto that weakens or breaks the bond created by the weld between the buttress and the tissue contacting surface of the surgical stapling apparatus, releasing the buttress therefrom. Thus, the present disclosure describes surgical buttresses, surgical stapling apparatus supporting said surgical buttresses, and methods and mechanisms for using the same.

It should be understood that a variety of surgical stapling apparatus may be utilized with a surgical buttress of the present disclosure. For example, linear stapler configurations may be utilized, such as, for example those including Duet TRS™ reloads and staplers with Tri-Staple™ technology, available through Covidien, which maintain a principal place of business at 555 Long Wharf Drive, North Haven, Conn. 06511, and transverse anastomosis staplers, such as, for example, EEA™, CEEA™, GIA™, EndoGIA™, and TA™, also available through Covidien. It should also be appreciated that the principles of the present disclosure are equally applicable to surgical staplers having alternate configurations, such as, for example, end-to-end anastomosis staplers having a circular cartridge and anvil (see, e.g., commonly owned U.S. Pat. No. 5,915,616, entitled "Surgical Fastener Applying Apparatus," the entire content of which is incorporated herein by this reference); laparoscopic staplers (see, e.g., commonly owned U.S. Pat. Nos. 6,330,965 and 6,241,139, each entitled "Surgical Stapling Apparatus," the entire contents of each of which being incorporated herein by this reference); and transverse anastomosis staplers (see, e.g., commonly owned U.S. Pat. Nos. 5,964,394 and 7,334,717, each entitled "Surgical Fastener Applying Apparatus", the entire contents of each of which being incorporated herein by this reference).

Embodiments of the presently disclosed surgical buttress and surgical stapling apparatus will now be described in detail with reference to the drawing figures wherein like reference numerals identify similar or identical elements. In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse, or other care provider and may include support personnel.

Referring now to FIG. 1, there is disclosed an exemplary surgical stapling apparatus or surgical stapler 10 for use in stapling tissue and applying a buttress material or surgical buttress to the tissue. Surgical stapling apparatus 10 generally includes a handle 12 having an elongate tubular member 14 extending distally from handle 12. A jaw assembly 16 is mounted on a distal end 18 of elongate tubular member 14. Jaw assembly 16 includes a staple clinching anvil jaw member 20 and a receiving jaw member 22 configured to receive a staple cartridge 32 (see FIG. 2A). Jaw assembly 16 may be permanently affixed to elongate tubular member 14 or may be detachable and thus replaceable with a new jaw assembly 16. Staple clinching anvil jaw member 20 is movably mounted on distal end 18 of jaw assembly 16 and is movable between an open position spaced apart from staple cartridge jaw member 22 to a closed position substantially adjacent staple cartridge jaw member 22.

Surgical stapling apparatus 10 further includes a trigger 33, as seen in FIG. 1, movably mounted on handle 12. Actuation of trigger 33 initially operates to move anvil jaw member 20 from the open to the closed position relative to staple cartridge jaw member 22 and subsequently actuates surgical stapling apparatus 10 to apply lines of staples to tissue. In order to properly orient jaw assembly 16 relative to the tissue to be stapled, surgical stapling apparatus 10 is additionally provided with a rotation knob 34 mounted on handle 12. Rotation of rotation knob 34 relative to handle 12 rotates elongate tubular member 14 and jaw assembly 16 relative to handle 12 so as to properly orient jaw assembly 16 relative to the tissue to be stapled.

Figure 6:
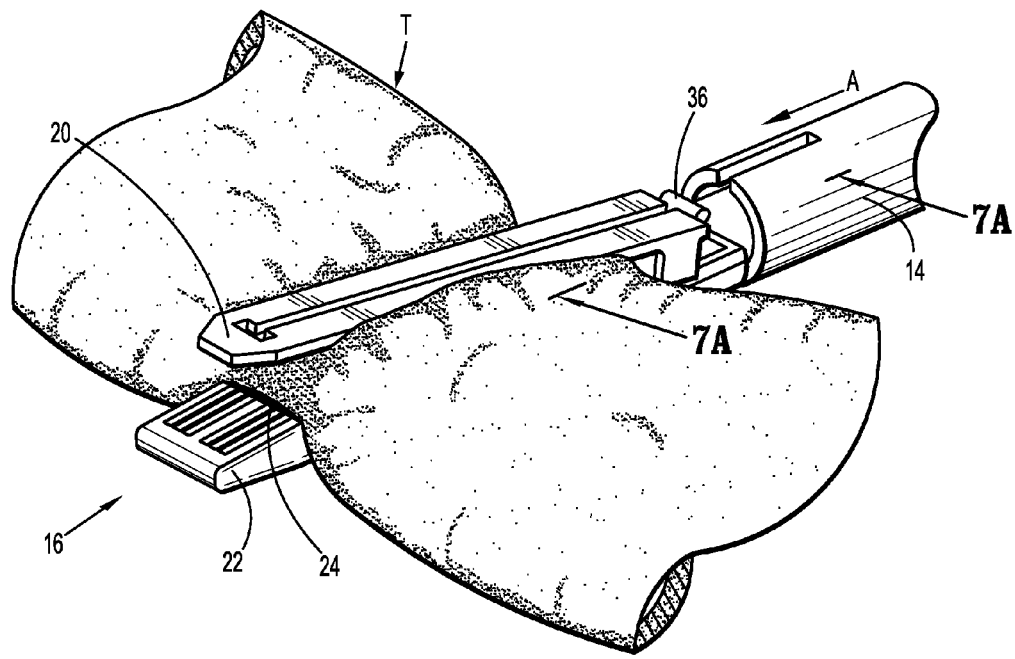
FIG. 6 is a perspective view of a distal end of the surgical stapling apparatus of FIG. 1, shown in use positioned about a tissue section.
Figure 7B:
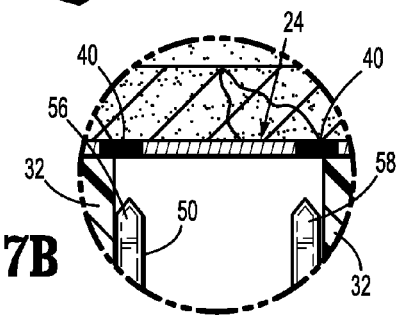
FIG. 7B is an enlarged area of detail depicted in FIG. 7A.
Figure 7A:
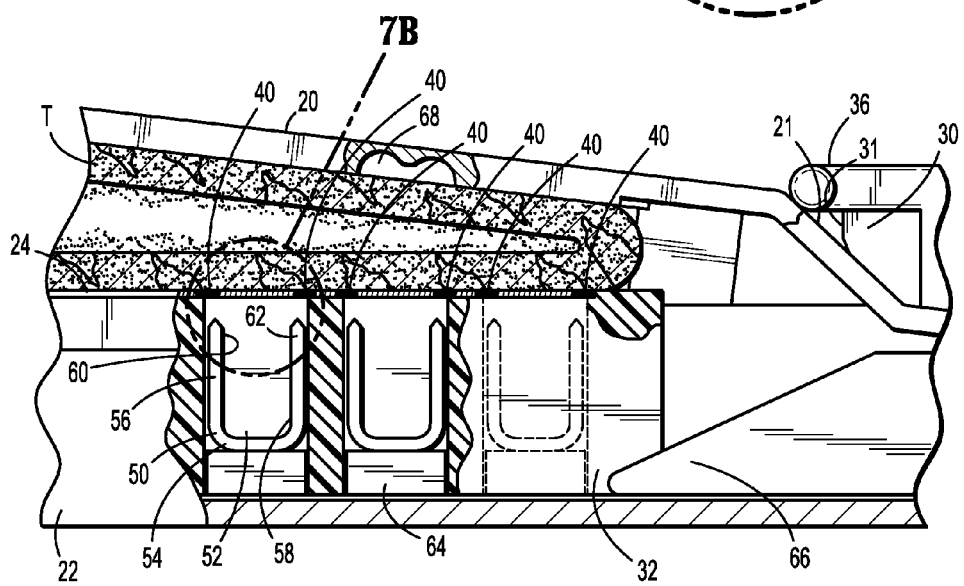
FIG. 7A is a cross-sectional view taken along line 7A-7A of FIG. 6.

A driver 36, as seen in FIGS. 6 and 7A, is provided to move anvil jaw member 20 between the open and closed positions relative to staple cartridge jaw member 22. Driver 36 moves through a longitudinal slot 38 (FIG. 1) formed in anvil jaw member 20. A knife 30 with knife blade 31 is associated with driver 36 to cut tissue captured between anvil jaw member 20 and staple cartridge jaw member 22 as driver 36 passes through slot 38.

Reference may be made to commonly owned U.S. Pat. Nos. 5,915,616, 6,330,965, and 6,241,139, referenced above, for a detailed discussion of the construction and operation of surgical stapling apparatus 10.

Staple clinching anvil jaw member 20 and/or staple cartridge jaw member 22 may be provided with a surgical buttress 24. It should be understood that a surgical buttress 24 may be associated with the staple cartridge jaw member 22, the anvil jaw member 20, and/or the staple cartridge 32. Surgical buttress 24 is provided to reinforce and seal the lines of staples applied to tissue by surgical stapling apparatus 10. Surgical buttress 24 may be configured into any shape, size, or dimension suitable to fit any surgical stapling, fastening, or firing apparatus.

Surgical buttress 24 is fabricated from a biocompatible material which is a bioabsorbable or non-absorbable, natural or synthetic material. It should of course be understood that any combination of natural, synthetic, bioabsorbable, and non-bioabsorbable materials may be used to form the surgical buttress.

The surgical buttress 24 may be porous, non-porous, or combinations thereof. It is also envisioned that surgical buttress 24 described herein may contain a plurality of layers in which any combination of non-porous and porous layers may be configured as discussed further below. For example, surgical buttress may be formed to include multiple non-porous layers and porous layers that are stacked in an alternating manner. In another example, surgical buttress may be formed in a "sandwich-like" manner wherein the outer layers of the surgical buttress include porous layers and the inner layers are non-porous layers. It is further envisioned that non-porous and porous layers may be positioned in any order relative to the tissue contacting surfaces of the staple cartridge jaw member and the anvil jaw member. Examples of multilayered surgical buttresses are disclosed in U.S. Patent Application Publication No. 2009/0001122 filed Jun. 27, 2007, entitled "Buttress and Surgical Stapling Apparatus," the entire disclosure of which is incorporated by reference herein.

Some non-limiting examples of materials from which non-porous and/or porous layers of surgical buttress 24 may be made include, but are not limited to, poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends, and combinations thereof.

In embodiments, natural biological polymers are used in forming a non-porous and/or porous layer of the surgical buttress. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, chitan, chitosan, and combinations thereof. In addition, the natural biological polymers may be combined with any of the other polymeric materials described herein to produce a non-porous layer of the surgical buttress.

In embodiments, amorphous polymers, e.g., thermoplastics, are utilized to form the surgical buttress of the present disclosure. Amorphous polymers melt gradually over a range of temperatures and include, for example, acrylonitrile-butadiene-styrene, acrylic, butadiene-styrene, polycarbonate, polyetherimide, polythalamide, polystyrene, polysulfone, polyvinyl chloride, and styrene-acrylonitrile copolymer. In embodiments, semi-crystalline materials such as nylon, polyethylene, and polypropylene, may be utilized alone or in combination with other materials to form a surgical buttress.

The use of non-porous layer(s) in the surgical buttress may enhance the ability of the surgical buttress to resist tears and perforations during the manufacturing, shipping, handling, and stapling processes. Also, the use of a non-porous layer in the surgical buttress may retard or prevent tissue ingrowth from surrounding tissues thereby acting as an adhesion barrier and preventing the formation of unwanted scar tissue. Thus, in embodiments, the non-porous layer(s) of the surgical buttress may possess anti-adhesion properties.

A non-porous layer of the surgical buttress may be formed using techniques within the purview of those skilled in the art, such as casting, molding, and the like.

Any of the porous layers of the surgical buttress may have openings or pores over at least a portion of a surface thereof. As described in more detail below, suitable materials for forming a porous layer include, but are not limited to, fibrous structures (e.g., knitted structures, woven structures, non-woven structures, etc.) and/or foams (e.g., open or closed cell foams). In embodiments, the pores may be in sufficient number and size so as to interconnect across the entire thickness of the porous layer. Woven fabrics, kitted fabrics, and open cell foam are illustrative examples of structures in which the pores can be in sufficient number and size so as to interconnect across the entire thickness of the porous layer. In embodiments, the pores may not interconnect across the entire thickness of the porous layer, but rather may be present at a portion thereof. Thus, in some embodiments, pores may be located on a portion of the porous layer, with other portions of the porous layer having a non-porous texture. Those skilled in the art reading the present disclosure will envision a variety of pore distribution patterns and configurations for the porous layer. Closed cell foam or fused non-woven materials are illustrative examples of structures in which the pores may not interconnect across the entire thickness of the porous layer.

Where a porous layer of the surgical buttress is fibrous, the fibers may be filaments or threads suitable for knitting or weaving or may be staple fibers, such as those frequently used for preparing non-woven materials. Suitable techniques for making fibrous structures are within the purview of those skilled in the art.

Where a porous layer of the surgical buttress is a foam, the porous layer may be formed using any method suitable to forming a foam or sponge including, but not limited to the lyophilization or freeze-drying of a composition. Suitable techniques for making foams are within the purview of those skilled in the art.

The origin and types of collagens that may be used to form the porous layer are the same as those indicated above for the non-porous layer. However, the oxidized or non-oxidized collagen may be lyophilized, freeze-dried, or emulsified in the presence of a volume of air to create a foam and then freeze-dried, to form a porous compress.

In embodiments, a porous layer of the surgical buttress may be made from denatured collagen or collagen which has at least partially lost its helical structure through heating or any other method. The term "denatured collagen" means collagen which has lost its helical structure. The collagen used for the porous layer as described herein may be native collagen or atellocollagen. The collagen may have been previously chemically modified by oxidation, methylation, succinylation, ethylation, or any other known process.

The porous layer(s) may enhance the ability of the surgical buttress to absorb fluid, reduce bleeding, and seal the wound. Also, the porous layer(s) may allow for tissue ingrowth to fix the surgical buttress in place.

As illustrated in the current embodiment and shown in FIG. 2A, the surgical buttress 24 is releasably attached to the staple cartridge 32 and/or the anvil jaw member 20 by welds 40 that bond the surgical buttress 24 to the inwardly facing or tissue contacting surface 23 of the staple cartridge 32 and/or the anvil jaw member 20, as discussed in detail below.

A buttress retention system 26 may also be incorporated into the staple cartridge 32 to aid in releasably securing the surgical buttress 24 to the staple cartridge 32. It is envisioned that buttress retention system 26 may additionally or alternatively be incorporated into anvil jaw member 20 such that a surgical buttress 24 may be releasably secured to anvil jaw member 20. Buttress retention system 26 may include means for attaching the surgical buttress 24 to the staple cartridge 32 and/or anvil jaw member 20, such as by pin 28 located on the staple cartridge 32 that is designed to releasably attach surgical buttress 24 to staple cartridge 32 via at least one hole 24a formed in the surgical buttress 24 that is shaped and designed to frictionally fit onto the pin 28. Other mechanical and/or chemical attachment means are within the purview of those skilled in the art and include, for example, the use of adhesives, sealants, glues, pins, tacks, tabs, clamps, channels, straps, protrusions, and combinations thereof.

Figure 2B:
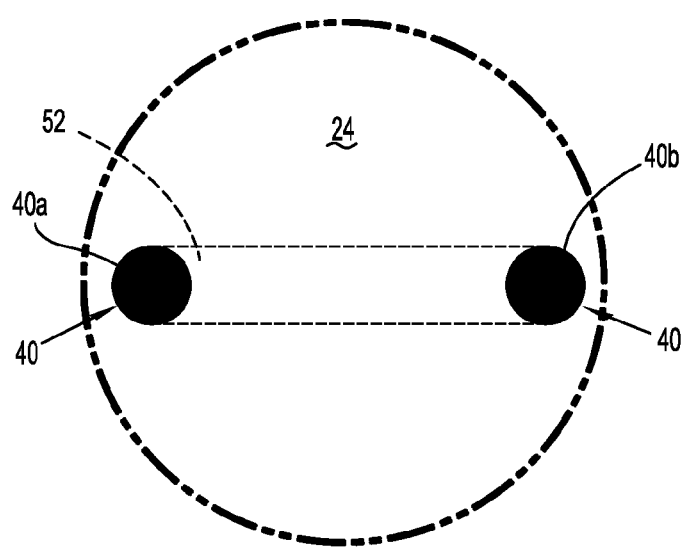
FIG. 2B is an enlarged area of detail depicted in FIG. 2A.
Figure 2A:
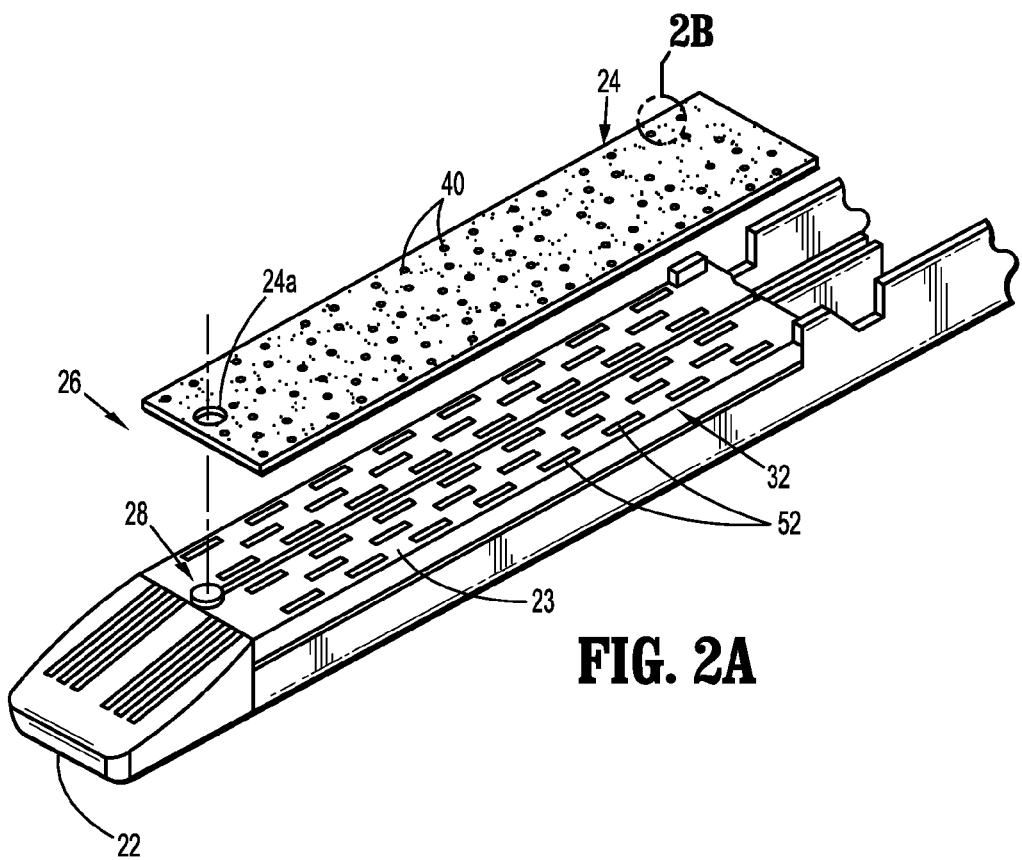
FIG. 2A is a perspective view, with parts separated, of a staple cartridge of the surgical stapling apparatus and of the surgical buttress of FIG. 1.

As illustrated in FIG. 2B, in conjunction with FIG. 2A, the welds 40 releasably attach the staple cartridge 32 and/or the anvil jaw member 20 in a manner which allows the surgical buttress 24 to be removed or released from the staple cartridge 32 and/or the anvil jaw member 20 upon penetration of the surgical buttress 24 by a surgical staple 50 (see FIG. 7A) or other fastening device. Accordingly, welds 40 are positioned at least partially over a staple pocket 52 (shown in phantom), as will be discussed in greater detail below.

The surgical buttress 24 may include a plurality of welds 40 attaching the surgical buttress 24 to the surgical stapling apparatus 10. As illustrated in FIG. 2A, welds 40 are positioned at least partially over a portion of all of the staple retaining slots 52 of the tissue contacting surface 23 of the staple cartridge 32.

As seen in FIG. 2B, in an embodiment, surgical buttress 24 may be secured to the tissue contacting surface 23 of staple cartridge 32 by welds 40 wherein a pair of welds 40A, 40B are provided for, or associated with, each staple retaining slot 52. In particular, a first weld 40A may secure surgical buttress 24 to the tissue contacting surface 23 of the staple cartridge 32 at a location near a distal end of staple retaining slot 52 wherein at least a portion of first weld 40A extends across a distal portion of staple retaining slot 52 such that at least a portion (e.g., a staple leg) of a surgical staple 50 (FIG. 7A), disposed within staple retaining slot 52, will at least impact or penetrate the first weld 40A and facilitate the release of first weld 40A from the tissue contacting surface 23 of staple cartridge 32 upon a firing of surgical stapling apparatus 10.

Similarly, as seen in FIG. 2B, a second weld 40B may secure surgical buttress 24 to the tissue contacting surface 23 of the staple cartridge 32 at a location near a proximal end of staple retaining slot 52 wherein at least a portion of second weld 40B extends across a proximal portion of staple retaining slot 52 such that at least a portion (e.g., a staple leg) of surgical staple 50, disposed within staple retaining slot 52, will at least impact or penetrate the second weld 40B and facilitate the release of second weld 40B from the tissue contacting surface 23 of staple cartridge 32 upon a firing of surgical stapling apparatus 10.

As can be appreciated from the foregoing description, in embodiments, first and second welds 40A, 40B are aligned with an ejection path of the legs of surgical staple 50. While a pair of welds 40A, 40B have been shown associated with each staple retaining slot 52, it is contemplated that a single weld may be associated with each staple retaining slot 52 or that fewer than all the staple retaining slots 52 will have a weld 40 associated therewith.

Additionally, it is contemplated that weld(s) 40 may be disposed at any location along the length of staple retaining slot 52.

Figure 3A:
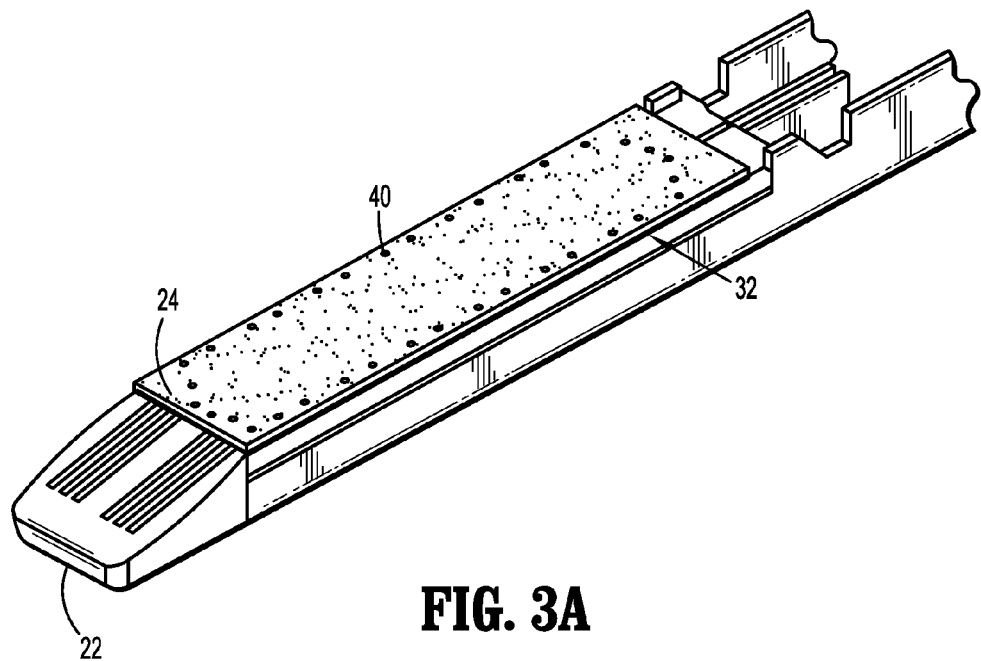
FIGS. 3A and 3B are perspective views of a staple cartridge of the surgical stapling apparatus and of a surgical buttress in accordance with other embodiments of the present disclosure.
Figure 3B:
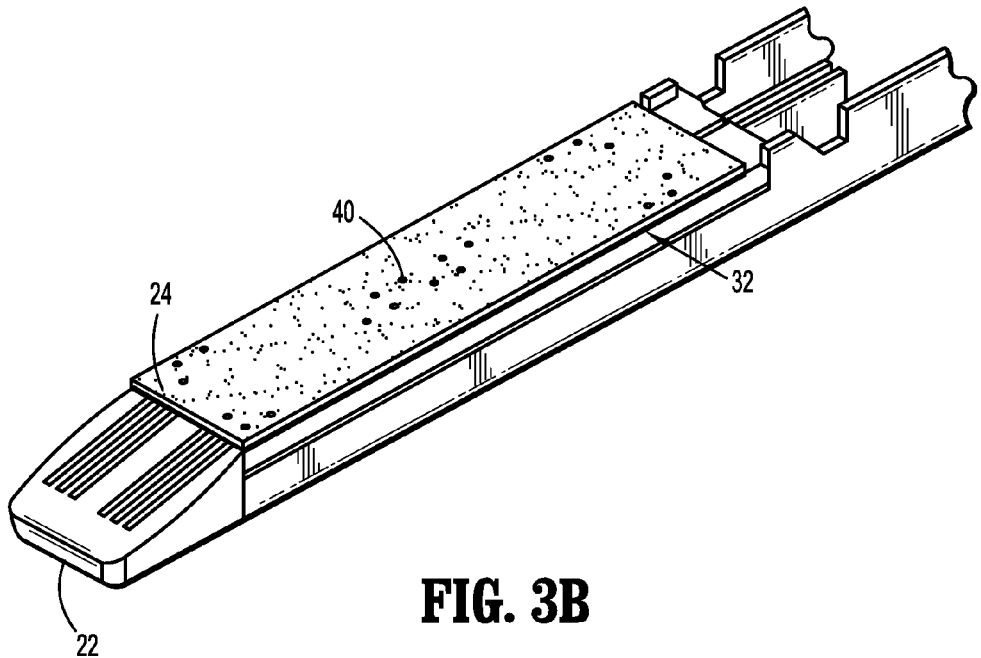

In embodiments, it is contemplated that the welds 40 may be distributed in a systematic or random pattern. Other configurations are also envisioned, such as those shown in FIGS. 3A and 3B. As illustrated in FIG. 3A, welds 40 are positioned around the perimeter of the surgical buttress 24. FIG. 3B illustrates welds 40 spaced about the surgical buttress 24 to facilitate passage of surgical stapling apparatus 10 into the body of a patient without risk of tearing or wrinkling of the surgical buttress 24 as surgical stapling apparatus 10 is inserted into and manipulated within the body of a patient. It is envisioned that the number of welds, weld size, and weld spacing can be varied to optimize the attachment of the surgical buttress to the surgical stapling apparatus, as well as to minimize the detachment force required during firing.

With reference now to FIGS. 4A and 4B, an ultrasonic welding assembly 1000, or the like, is illustrated for attaching a surgical buttress 24 to a staple cartridge 32. The staple cartridge 32 and surgical buttress 24 are placed within a channel 1022 of base 1020 of welding assembly 1000. Welding assembly 1000 includes an ultrasonic device 1010 operably connected to a generator (not shown) for ultrasonically vibrating a die 1012 extending from ultrasonic device 1010. Die 1012 defines a patterned surface 1014 including projections 1016 for forming the individual welds 40 on the surgical buttress 24. Projections 1016 provide small contact surfaces so that the energy delivered by ultrasonic device 1010 is concentrated over a small area. The projections 1016 may be any shape, such as, for example, rectangular, triangular, circular, oval, and other polygons and irregular shapes and combinations thereof.

In one embodiment, welding assembly 1000 is operatively mounted on a press assembly (not shown) for approximating die 1012 of welding assembly 1000 towards and away from base 1020. Alternatively, welding assembly 1000 may be securely mounted relative to base 1020 and base 1020 may be raised and lowered to approximate base 1020 towards and away from die 1012. The downward pressure exerted on the surgical buttress 24 by the patterned die 1012, indicated by the arrows in FIG. 4B, and the ultrasonic vibration of die 1012 causes the portions of the surgical buttress 24 and staple cartridge 32 that are in contact with each other to locally heat, and in some instances, begin to melt thereby fusing/bonding the surgical buttress 24 to the staple cartridge 32 by welds 40.

FIG. 5 illustrates another ultrasonic welding assembly 2000 that may be utilized to attach the surgical buttress 24 to the staple cartridge 32. Ultrasonic welding assembly 2000 includes a horn 2010 and an anvil 2020. Anvil 2020 is shaped as a cylindrical drum having raised projections 2022 for structuring the size and distribution of the welds 40.

The staple cartridge 32 and surgical buttress 24 are passed over anvil 2020 and mechanically worked by moving horn 2010 up and down via driving means 2012 into portions of buttress material 24 lying on projections 2022 with a frequency that lies within the ultrasonic range. Heat is generated in the worked areas of the surgical buttress 24 causing the surgical buttress 24 to melt and fuse/bond with the staple cartridge 32. Alternatively, the amount of heat generated may be higher to affect heating and melting of both the surgical buttress 24 and staple cartridge 32.

Any combination of steps as described above may be utilized to fuse/bond the surgical buttress 24 to the staple cartridge 32. Larger areas of the surgical buttress 24 may be sonically welded by providing additional horns or larger horns to the welding device 2000 or by using an anvil 2020 with larger projections, or, in embodiments, a flat anvil.

In embodiments, the staple cartridge 32 and surgical buttress 24 may be fabricated from the same material, or from materials with similar melting temperatures to achieve welds 40. Alternatively, different combinations of compatible materials for staple cartridge 32 and surgical buttress 24 may be utilized to form welds 40.

As illustrated in FIG. 6, during use of surgical stapling apparatus 10, the anvil jaw member 20 and the staple cartridge jaw member 22 including a staple cartridge 32, which has been loaded with a surgical buttress 24 such as by an ultrasonic welding process as described above, are positioned on either side of the surgical site where adjacent layers of tissue "T" are to be fastened to one another.

As best shown in FIG. 7A, staple cartridge 32 includes surgical staples 50 positioned within individual staple pockets 52. Staples 50 are of a conventional type and include a backspan 54 having a pair of legs 56 and 58 extending from backspan 54. Legs 56 and 58 terminate in tissue penetrating tips 60 and 62, respectively. Pushers 64 are located within staple pockets 52 and are positioned between staples 50 and the path of a drive bar 66.

Surgical stapling apparatus 10 is initially actuated by movement of trigger 33 relative to handle 12 (FIG. 1) causing driver 36 to move in the direction of arrow "A" (FIG. 6), and against sloped edge 21 of anvil jaw member 20 thereby causing anvil jaw member 20 to be moved to the closed position relative to staple cartridge jaw member 22. As drive bar 66 advances distally within staple cartridge 32, drive bar 66 urges pushers 64 upwardly against backspan 54 of staples 50 driving legs 56 and 58 of staples 50 (which are aligned with respective welds 40 as detailed in FIG. 7B) through at least a portion of the welds 40, the surgical buttress 24, tissue "T", and towards staple forming pockets 68 in anvil jaw member 20. Tissue penetrating tips 60 and 62 of staple legs 56 and 58 are bent within staple forming pockets 68 in anvil jaw member 20 with backspan 54 securing surgical buttress 24 against tissue "T". The force of the staples 50 being fired breaks the bonds between the surgical buttress 24 and the staple cartridge 32, thereby releasing the surgical buttress 24 from the staple cartridge 32 of the surgical stapling apparatus 10.

Upon full actuation of surgical stapling apparatus 10, a knife 30 associated with surgical stapling apparatus 10 and carried by driver 36 may be utilized to cut tissue "T", as well as surgical buttress 24 between the rows of now formed staples 50. Upon movement of anvil jaw member 20 to the open position spaced apart from staple cartridge jaw member 22, surgical buttress 24 finishes pulling away from anvil jaw member 20 and staple cartridge 32 of staple cartridge jaw member 22.

Figure 8:
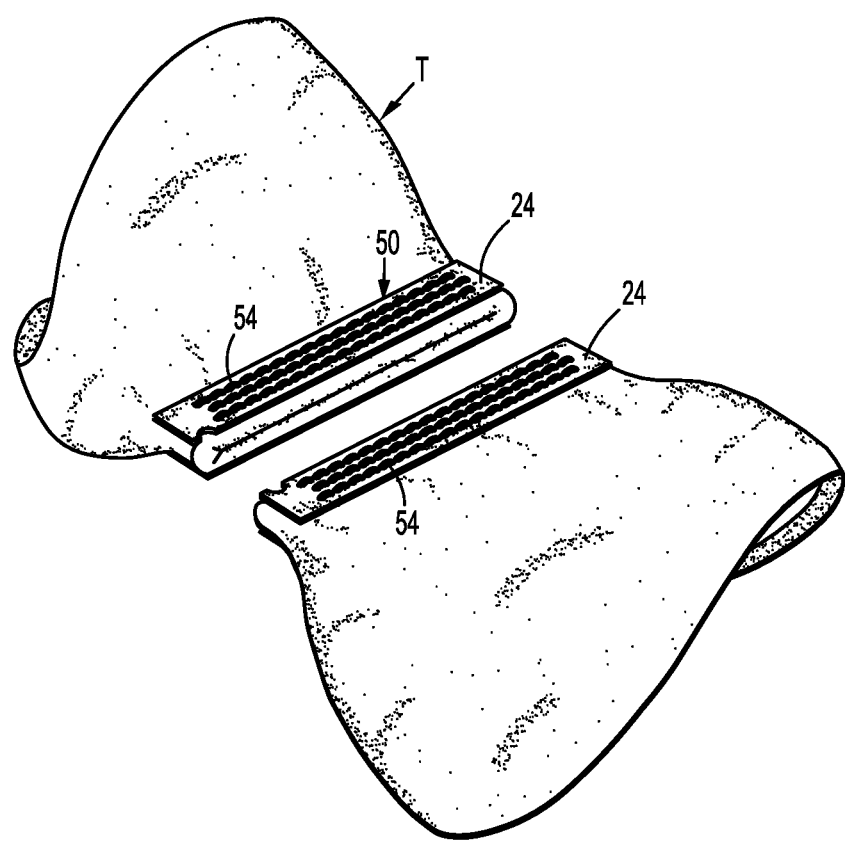
FIG. 8 is a perspective view of the stapled and divided tissue section of FIG. 6.

The resulting tissue "T", divided and stapled closed with staples 50, is illustrated in FIG. 8. Specifically, surgical buttress 24 is secured against tissue "T" by backspans 54 of staples 50. Thus, surgical buttress 24 is stapled to tissue "T" thereby sealing and reinforcing the staple lines created by staples 50.

Figure 9A:
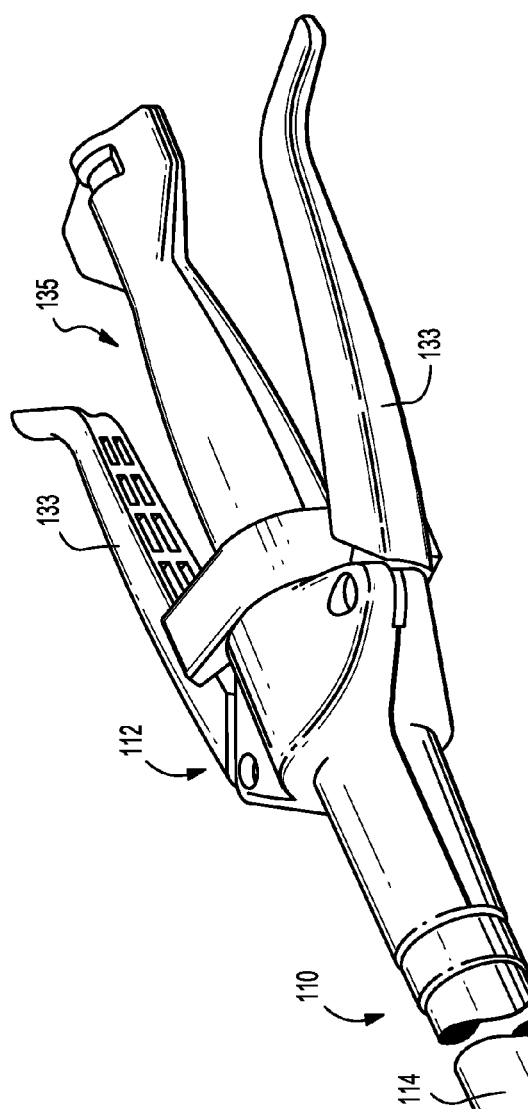
FIG. 9A is a perspective view of an illustrative embodiment of a surgical stapling apparatus in accordance with another embodiment of the present disclosure.
Figure 9B:
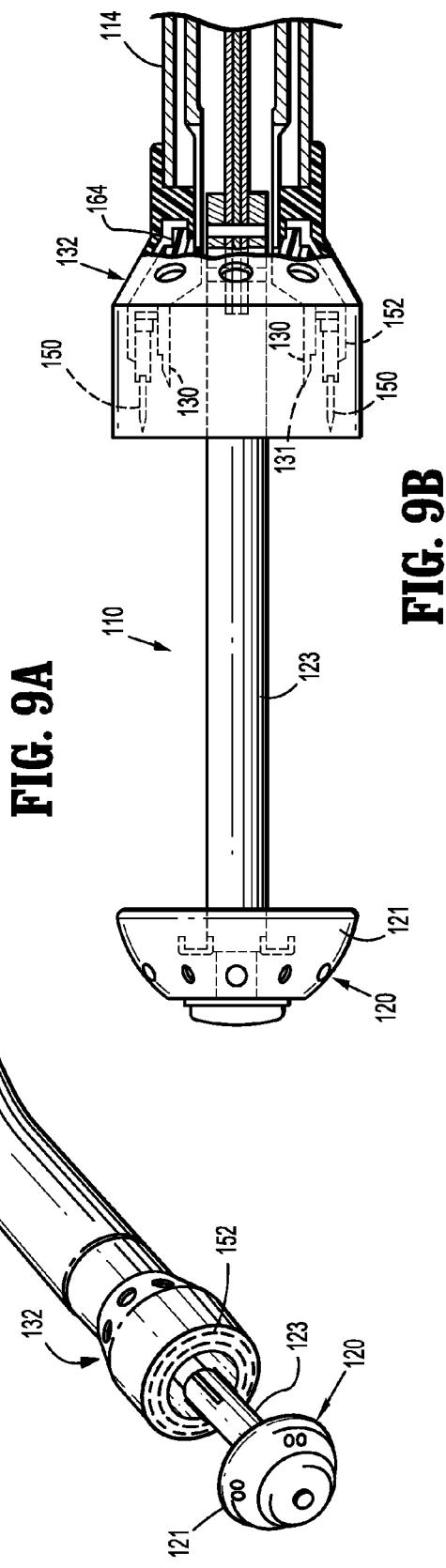
FIG. 9B is a cross-sectional view of the surgical stapling apparatus of FIG. 9A.

Referring now to FIGS. 9A and 9B, an annular surgical stapling apparatus 110, for use with a surgical buttress 124 of the present disclosure, is shown. Surgical stapling apparatus 110 includes a handle assembly 112 having at least one pivotable actuating handle member 133, and an advancing member 135. Extending from handle member 112, there is provided a tubular body portion 114 which may be constructed so as to have a curved shape along its length. Body portion 114 terminates in a staple cartridge assembly 132 which includes a pair of annular arrays of staple receiving slots 152 having a staple 150 disposed in each one of staple receiving slots 152. Positioned distally of staple cartridge assembly 132 there is provided an anvil assembly 120 including an anvil member 121 and a shaft 123 operatively associated therewith for removably connecting anvil assembly 120 to a distal end portion of stapling apparatus 110.

Staple cartridge assembly 132 may be fixedly connected to the distal end of tubular body portion 114 or may be configured to concentrically fit within the distal end of tubular body portion 114. Staple cartridge assembly 132 includes a staple pusher 164 including a proximal portion having a generally frusto-conical shape and a distal portion defining two concentric rings of peripherally spaced fingers (not shown), each one of which is received within a respective staple receiving slot 152.

A knife 130, substantially in the form of an open cup with the rim thereof defining a knife blade 131, is disposed within staple cartridge assembly 132 and mounted to a distal surface of a staple pusher 164. The knife 130 is disposed radially inward of the pair of annular arrays of staples 150. Accordingly, in use, as the staple pusher 164 is advanced, the knife 130 is also advanced axially outward.

Figure 10B:
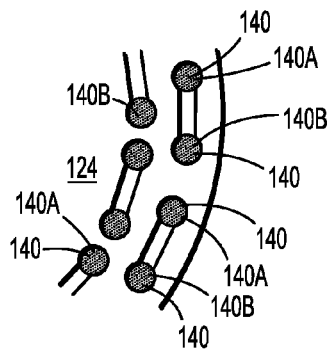
FIG. 10B is an enlarged area of detail depicted in FIG. 10A.
Figure 10A:
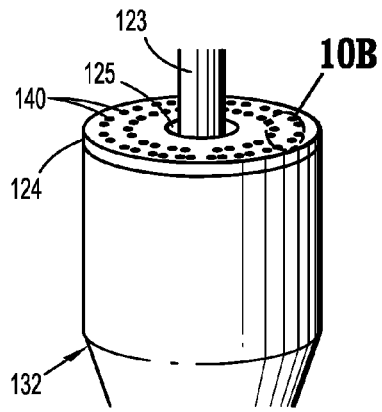
FIG. 10A is a perspective view of an illustrative embodiment of the staple cartridge of the surgical stapling apparatus of FIG. 9A including a surgical buttress in accordance with an embodiment of the present disclosure.

As seen in FIG. 10A, a surgical buttress 124 is releasably attached to the staple cartridge 132 by welds 140 that bond the surgical buttress 124 thereto. It is envisioned that the surgical buttress 124 may be additionally or alternatively attached to the anvil assembly 120. Surgical buttress 124 is provided in an annular configuration and includes an aperture 125 to receive shaft 123 of anvil assembly 120 therethrough. As illustrated, the welds 140 are in an annular configuration such that they at least partially overlay and extend across the staple retaining slots 152.

As shown in FIG. 10B, surgical buttress 124 may be secured to the staple cartridge 32 by welds 140 wherein a pair of welds 140A, 140B are provided for, or associated with, each staple retaining slot 152 (FIG. 9A). In particular, a first weld 140A may secure surgical buttress 124 to the staple cartridge 132 such that at least a portion of first weld 140A extends across a portion of a staple retaining slot 152. In such a configuration, at least a portion (e.g., a staple leg) of a surgical staple (not shown) disposed within staple retaining slot 152, will at least impact or penetrate the first weld 140A and facilitate the release of first weld 140A from the staple cartridge 132 upon a firing of surgical stapling apparatus 110. Similarly, a second weld 140B may secure surgical buttress 124 to the staple cartridge 132 such that at least a portion of second weld 140B extends across the staple retaining slot 152.

It is envisioned that other configurations may be utilized to retain the surgical buttress 124 to the staple cartridge 132, such as providing the welds 140 in either the inner or outer annular row of staple retaining slots 152, or alternating the welds 140 between the staple retaining slots 152, among other arrangements within the purview of those skilled in the art.

Figure 12:
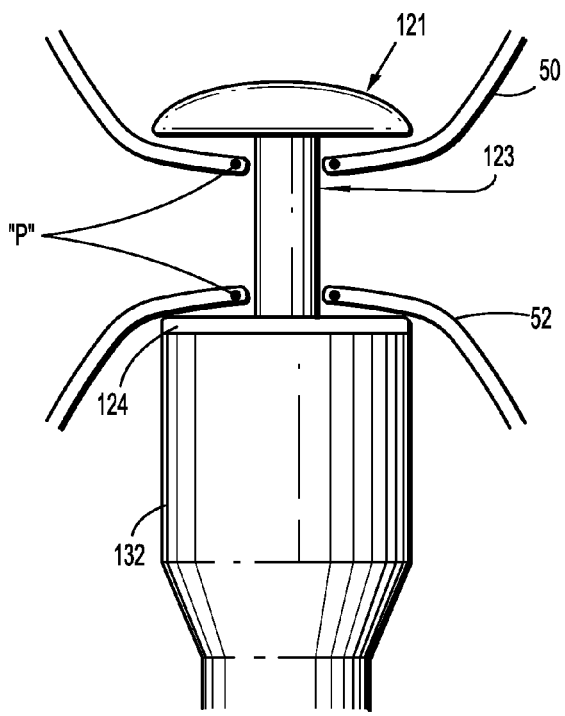
FIG. 12 is a schematic perspective view of the intestinal area of FIG. 11, illustrating the anvil rod mounted to the surgical stapling apparatus.
Figure 11:
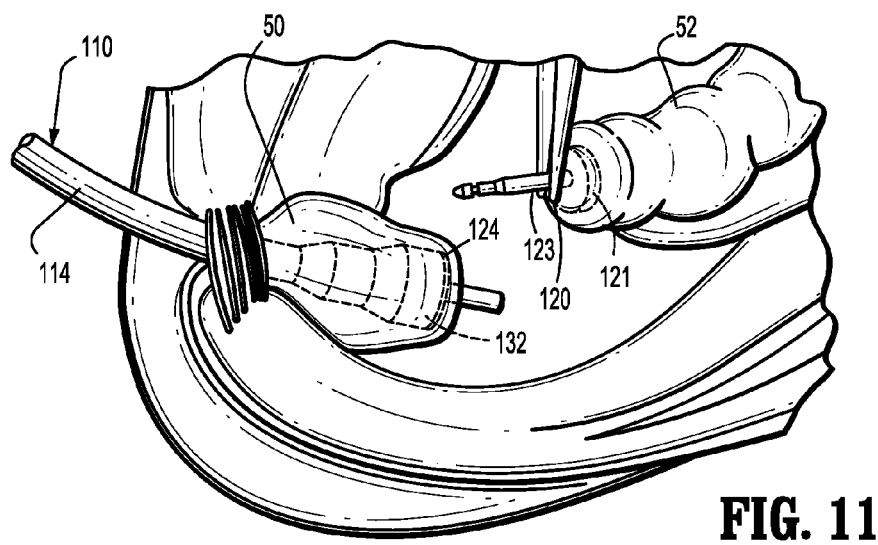
FIG. 11 is perspective view of an intestinal area of a patient, illustrating a method of positioning the anvil rod and staple cartridge of the surgical stapling apparatus of FIGS. 9A, 9B, and 10 within the intestinal area.

Surgical stapling apparatus 110 and detachable anvil assembly 120 are used in an anastomosis procedure to effect joining of intestinal sections 50 and 52. The anastomosis procedure is typically performed using minimally invasive surgical techniques including laparoscopic means and instrumentation. At the point in the procedure shown in FIG. 11, a diseased intestinal section has been previously removed, anvil assembly 120 has been applied to the operative site either through a surgical incision or transanally and positioned within intestinal section 52, and tubular body portion 114 of surgical stapling apparatus 110 has been inserted transanally into intestinal section 50. Intestinal sections 50 and 52 are also shown temporarily secured about their respective components (e.g., shaft 123 of anvil assembly 120, and the distal end of tubular body portion 114) by conventional means such as a purse string suture "P", as illustrated in FIG. 12.

Thereafter, the clinician maneuvers anvil assembly 120 until the proximal end of shaft 123 is inserted into the distal end of tubular body portion 114 of surgical stapling apparatus 110, wherein the mounting structure (not shown) within the distal end of tubular body portion 114 engages shaft 123 to effect the mounting. Anvil assembly 120 and tubular body portion 114 are then approximated to approximate intestinal sections 50, 52. Surgical stapling apparatus 110 is then fired. The force of the staples (not shown) being fired breaks the bonds between the surgical buttress 124 and the staple cartridge 132 created by welds 140 thereby releasing the surgical buttress 124 from the staple cartridge 132, and effecting stapling of intestinal sections 50, 52 to one another. A knife (not shown) cuts the portion of tissue and surgical buttress 124 disposed radially inward of the knife, to complete the anastomosis. In embodiments in which the surgical buttress 124 is disposed radially outward of the knife, only tissue is transected by the knife blade.

Figure 13:
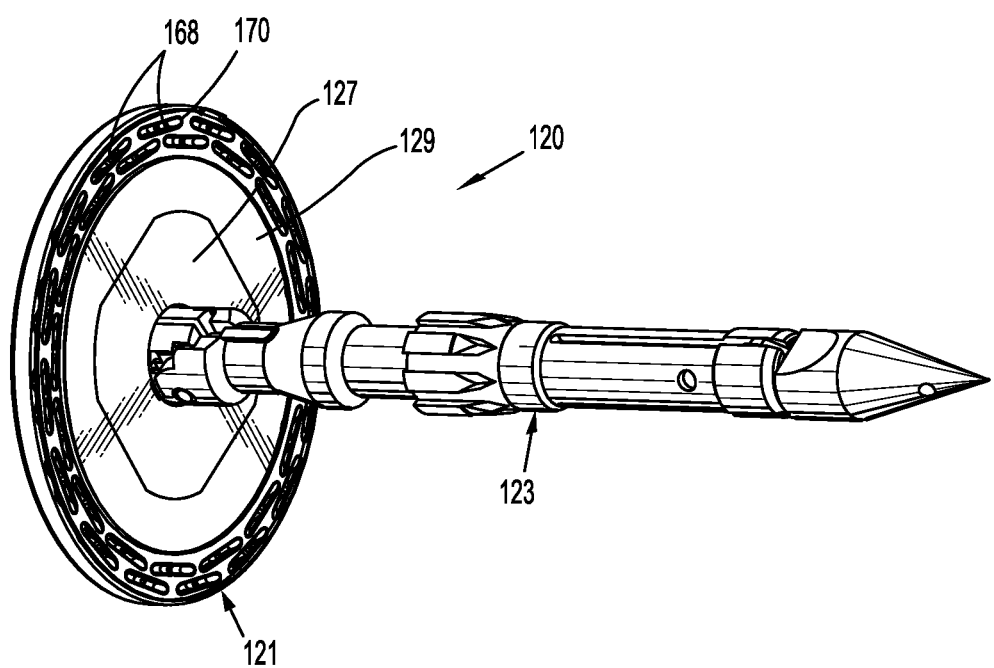
FIG. 13 is a perspective view of an anvil assembly including a polymeric insert in accordance with an embodiment of the present disclosure.

Referring now to FIG. 13, anvil assembly 120 is illustrated including a polymeric insert 170. Typically the anvil assembly 120 is formed from a metal, such as stainless steel, and thus, a polymeric insert 170 may be utilized for attachment of a surgical buttress (not shown) thereto. Anvil head 121 includes a plurality of staple forming pockets 168 extending radially around an outer periphery of the tissue contacting surface 127 of the anvil head 121 for receiving and deforming staples (not shown). A cut ring 129 is disposed radially inward of the staple forming pockets 168 such that the knife blade (not shown) abuts and/or penetrates the cut ring 129 during firing of the surgical stapling apparatus to enhance cutting of tissue. Typically, cut ring 129 is formed from a soft material, e.g., polyethylene, to allow some degree of knife penetration into the cut ring 129.

Polymeric insert 170 may be fabricated from the same material as the surgical buttress, or alternatively, from a material compatible with the surgical buttress. The polymeric insert 170 may be attached to the tissue contacting surface 127 of the anvil head 121 utilizing methods within the purview of those skilled in the art, such as by utilizing adhesives or overmolding the polymeric insert 170 over the tissue contacting surface 127 of the anvil head 121. A surgical buttress is attached to the polymeric insert 170 by welds that bond the surgical buttress to thereto, such that the welds at least partially overlay and extend across the staple forming pockets 168 along an ejection path of a staple as described above. In some embodiments, such as embodiments including a surgical buttress associated with the cartridge assembly, a surgical buttress may be attached to a portion of cut ring 129 (e.g., by welding) such that release of the surgical buttress associated with the cartridge assembly is provided by firing of the staples and release of the surgical buttress associated with the anvil assembly is accomplished by knife blade cutting.

Figure 14:
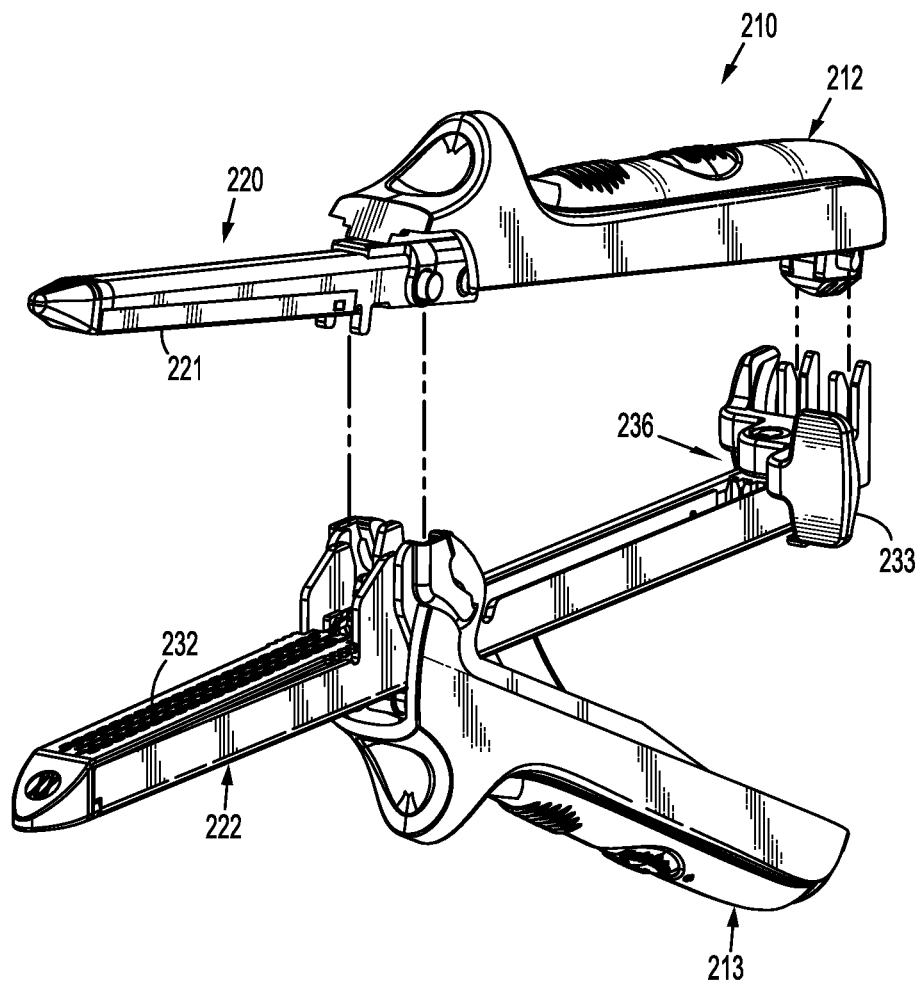
FIG. 14 is a perspective view of another illustrative embodiment of a surgical stapling apparatus for use with a surgical buttress of the present disclosure.

The surgical buttress of the present disclosure may be adapted for use with other surgical stapling apparatus in accordance with the present disclosure, such as the surgical stapling apparatus shown and described in U.S. Pat. No. 7,334,717, entitled "Surgical Fastener Applying Apparatus," the entire content of which is incorporated herein by reference. As illustrated in FIG. 14, surgical stapling apparatus 210 includes an anvil receiving section 220 and a cartridge receiving section 222. A surgical buttress (not shown) may be welded to at least one of an anvil 221 coupled to the anvil receiving section 220, a staple cartridge 232 coupled to the cartridge receiving section 222, or both, as discussed above. The anvil receiving section 220 and the cartridge receiving section 222 are pivotally connected via handles 212, 213 for approximation during use. Following approximation of the anvil receiving section 220 and the cartridge receiving section 222, the surgical stapling apparatus 210 is fired by driving a firing slide 236 distally through the advancement of a firing lever 233. Distal movement of the firing slide 233 causes a plurality of cam bars to engage camming surfaces that interact with a plurality of pushers to expel a plurality of surgical staples (not shown) from the cartridge receiving section 222. The force of the staples being fired breaks the bonds between the surgical buttress and the staple cartridge, for example, created by welds between the surgical buttress and the staple cartridge, thereby releasing the surgical buttress from the staple cartridge. The staples are positioned on either side of a track which guides a knife (not shown) during longitudinal movement to thereby sever tissue along a cut-line.

Figure 15:
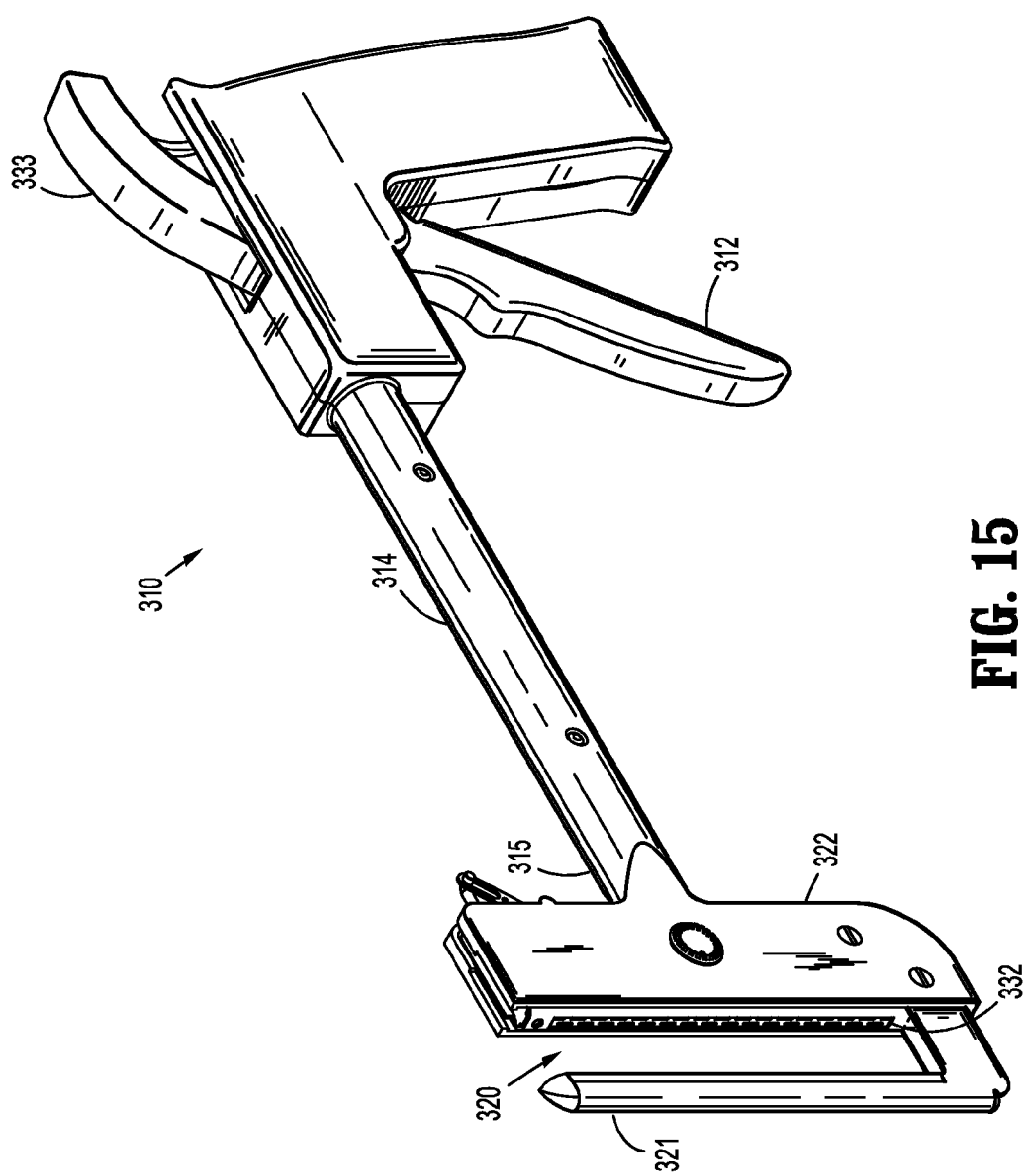
FIG. 15 is a perspective view of yet another illustrative embodiment of a surgical stapling apparatus for use with a surgical buttress of the present disclosure.

The surgical buttress of the present disclosure may also be adapted for use with a transverse surgical stapling apparatus 310, as illustrated in FIG. 15. An exemplary transverse surgical stapling apparatus is shown and described in U.S. Pat. No. 5,964,394, entitled "Surgical Fastener Applying Device," the entire content of which is incorporated herein by reference. The surgical stapling apparatus 310 includes an approximation lever 333, a movable handle 312, an elongated portion 314 that extends distally from the handle 312, and an arm 322 that extends from a distal end 315 of the elongated portion 314. The surgical stapling apparatus 310 further includes an anvil 321 that is orthogonally affixed to the arm 322, and a cartridge receiver 320 that is operatively coupled to the distal end 315 of the elongated portion 314 for retention of a staple cartridge 332. A surgical buttress (not shown) may be welded to at least one of the anvil 321, staple cartridge 332, or both as discussed above.

In embodiments, at least one bioactive agent may be combined with a surgical buttress of the present disclosure. The at least one bioactive agent may be disposed on a surface of the surgical buttress and/or impregnated therein. In these embodiments, the surgical buttress can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the surgical buttress in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Other bioactive agents which may be included as a bioactive agent in the surgical buttress of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

In embodiments, a reinforcement member may be positioned within or over a surgical buttress. In embodiments utilizing a multilayered surgical buttress, one or more reinforcement members may be positioned between, within, or at an external surface of a layer of the surgical buttress as are disclosed, for example, in U.S. Patent Application Publication No. 2009/0001122, reference above.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A staple cartridge for use with a surgical stapling apparatus, the staple cartridge comprising:
   a cartridge body;
   a plurality of staples disposed within the cartridge body, each staple including a crown and at least one leg depending from the crown;
   a tissue contacting surface of the cartridge body defining staple retaining slots, each staple retaining slot having a first end and a second end; and
   a buttress material secured to the cartridge body by a plurality of welds joining the buttress material to the tissue contacting surface,
   the plurality of welds being in registration with at least the first end and second end of a portion of the staple retaining slots of the tissue contacting surface such that the at least one leg of the staple impacts at least one of the plurality of welds when the staple is ejected from the staple retaining slot.

2. The staple cartridge of claim 1, wherein the staple retaining slots include a first staple retaining slot; and the buttress material being secured by a first weld and a second weld of the plurality of welds, the first weld being in registration with the first end of the first staple retaining slot, and the second weld being in registration with the second end of the first staple retaining slot.

3. The staple cartridge of claim 2, wherein the staple includes a pair of legs, the pair of legs impacting the first and second welds when the staple is ejected from the first staple retaining slot.

4. The staple cartridge of claim 1, wherein the plurality of welds is in registration with at least the first end and second end of each staple retaining slot of the tissue contacting surface.

5. The staple cartridge of claim 1, wherein the plurality of welds are distributed in a pattern over the tissue contacting surface.

6. The staple cartridge of claim 1, wherein the buttress material is porous.

7. The staple cartridge of claim 1, wherein a portion of the buttress material is non-porous.

8. The staple cartridge of claim 1, wherein the plurality of welds is a portion of the buttress material.

9. The staple cartridge of claim 1, wherein the staple retaining slots are arranged in an annular configuration.

10. The staple cartridge of claim 1, wherein the tissue contacting surface includes at least two rows of staple retaining slots.

11. The staple cartridge of claim 10, wherein the at least two rows of staple retaining slots are positioned in one of a linear configuration and an annular configuration.

12. A staple cartridge for use with a surgical stapling apparatus, the staple cartridge comprising:
a cartridge body having a tissue contacting surface defining staple retaining slots, each staple retaining slot having a first end and second end; and
a buttress material secured to the cartridge body by a plurality of welds joining the buttress material to the tissue contacting surface, the plurality of welds being in registration with at least the first end and the second end of a portion of the staple retaining slots.

13. The staple cartridge of claim 12, wherein the staple retaining slots include a first staple retaining slot; and
the buttress material being secured by a first weld and a second weld of the plurality of welds, the first weld being in registration with the first end of the first staple retaining slot, and the second weld being in registration with the second end of the first staple retaining slot.

14. The staple cartridge of claim 12, wherein the plurality of welds are in registration with at least the first end and the second end of each staple retaining slot of the tissue contacting surface.

15. The staple cartridge of claim 12, wherein the plurality of welds are distributed in a pattern over the tissue contacting surface.

16. The staple cartridge of claim 12, including a plurality of staples disposed within the cartridge body, wherein at least one of the plurality of staples impact at least one of the plurality of welds when the plurality of staples are ejected from the staple retaining slots.

17. The staple cartridge of claim 12, wherein the buttress material is porous.

18. The staple cartridge of claim 12, wherein a portion of the buttress material is non-porous.

19. The staple cartridge of claim 12, wherein the staple retaining slots are arranged in an annular configuration.

20. The staple cartridge of claim 12, wherein the tissue contacting surface includes at least two rows of staple retaining slots.

21. The staple cartridge of claim 20, wherein the at least two rows of staple retaining slots are positioned in one of a linear configuration and an annular configuration.

* * * * *